United States Patent [19]

Uthmann

[11] 4,385,631
[45] May 31, 1983

[54] CATHETER

[76] Inventor: Ulrich Uthmann, Schulstrasse 5, 6936 Haag, Fed. Rep. of Germany

[21] Appl. No.: 245,111

[22] Filed: Mar. 18, 1981

[30] Foreign Application Priority Data

Mar. 21, 1980 [DE] Fed. Rep. of Germany ....... 3010841

[51] Int. Cl.³ .............................................. A61M 5/32
[52] U.S. Cl. ...................................... 604/284; 604/53
[58] Field of Search .............. 128/349, 348, 350, 214, 128/214.2, 214.4, 221, DIG. 3

[56] References Cited

U.S. PATENT DOCUMENTS 3,804,097  4/1974  Rudie .............................. 128/350 R
4,069,814  1/1978  Clemens ..................... 128/214 R X
4,098,275  4/1978  Consalvo ......................... 128/214 R
4,134,402  1/1979  Mahurkar ....................... 128/214 R
4,314,555  2/1982  Sagae ............................... 128/214.4

*Primary Examiner*—Stephen C. Pellegrino
*Attorney, Agent, or Firm*—Max Fogiel

[57] ABSTRACT

A catheter for puncturing blood vessels, particularly for vein punctures for hemo-dialysis. A section is insertable through a puncture opening into a blood vessel and a hose line following thereafter. The arrangement is in form of a double catheter in which two single catheters are associated for relative lengthwise movement by means of a longitudinal guide.

13 Claims, 8 Drawing Figures

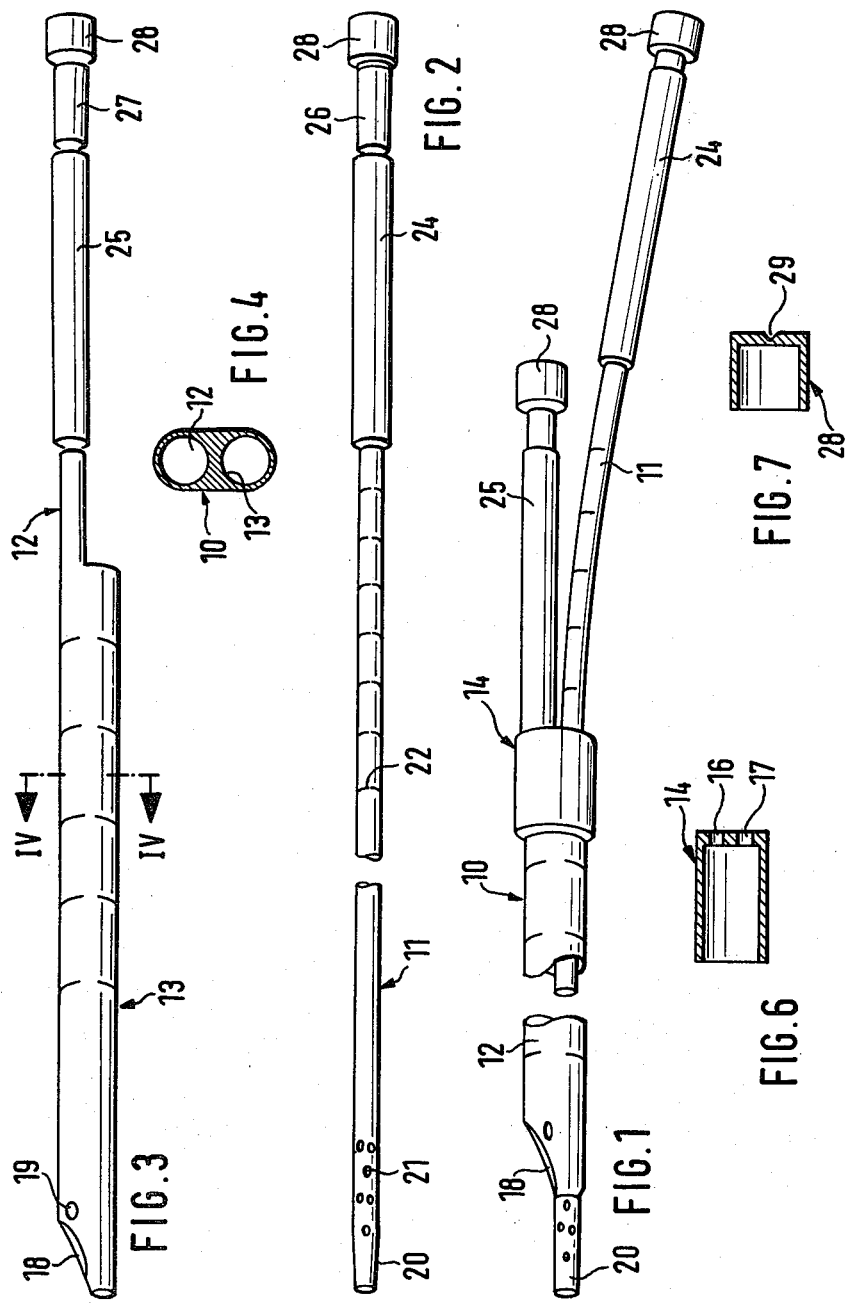

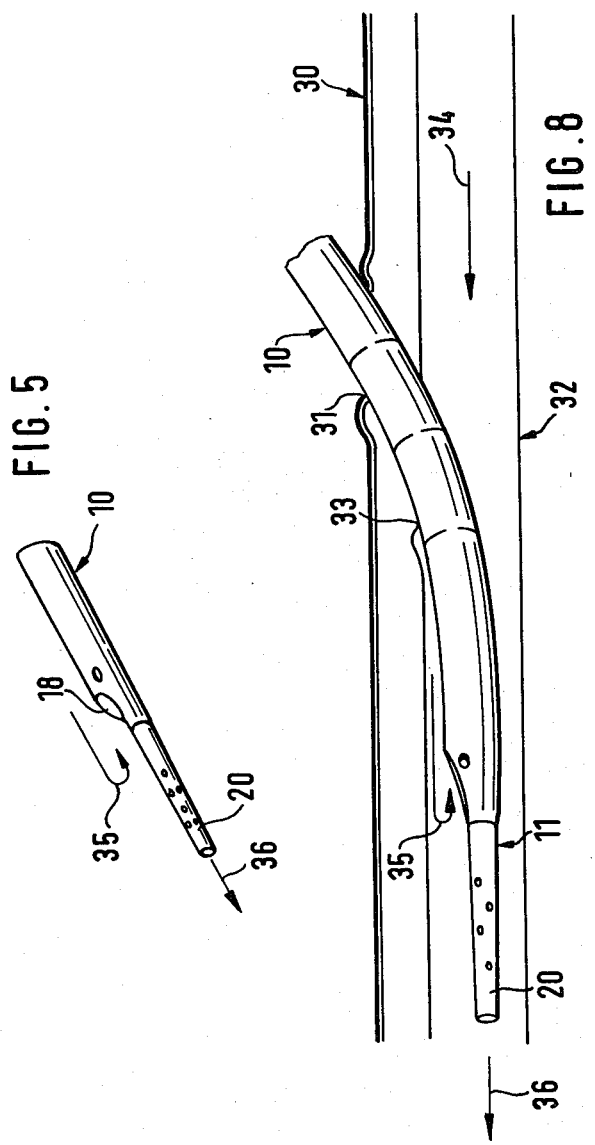

CATHETER

DESCRIPTION

The invention relates to a catheter for puncturing of blood vessels, especially for vein puncturing for hemodialysis, with a section insertable through a puncture opening into a blood vessel and a thereafter following hose line.

Catheters of this kind are known. As a rule they are flexible silicone hoses with possibly a special construction of the catheter tip, i.e. of the section which is insertable into a blood vessel through an appropriate puncture opening. Such catheters have already been used for vein punctures for venous hemo-dialysis. Two methods are known, namely the non-continuous dialysis with more or less pronounced hemostasis in the dialysis filter and the dialysis with two puncture locations and correspondingly two catheters, which assures a continuous blood flow.

Both methods have been found to be inadequate. Thus, in the non-continuous dialysis large quantities of pendulum blood occur, which naturally significantly reduces the efficiency of the dialysis. In the second method, which operates with two catheters which are introduced into a vein at two spaced-apart puncture locations, this disadvantage is avoided, insofar as the blood supply takes place at the puncture location which in flow direction is ahead of the blood removal location, but the requirement of a dual function of a large body vein results in an increased danger of thrombosis and infection.

In contradistinction, the invention is to create a catheter with which it is possible to eliminate the increased thrombosis- and infection danger of the second method and the occurrence of pendulum blood quantities which characterizes the first method. According to the invention this task is solved by the construction of the catheter as a double catheter in which the two individual catheters are arranged longitudinally movable relative to each other, by means of a longitudinal guide. The invention thus concerns a double-barrelled catheter which is movable relative to itself and with which it is possible to space the inlet puncture in the region of the catheter tip of the one catheter and the outlet opening of the other catheter, after insertion into a blood vessel, for example a vein, in the flow direction of the blood, in such a manner that the supply of blood takes place so far ahead of the blood removal in flow direction, that the blood returned into the vein does not move to the region of the blood removal location so that the occurrence of pendulum blood is avoided. This requires only one puncture, so that the dangers resulting from multiple punctures are also eliminated.

Advantageous embodiments are set forth in the dependent claims 2 to 11.

In an advantageous embodiment of the invention the longitudinal guide is a cuff surrounding and connected to—respectively of one piece with—the one individual catheter, in which the other individual catheter is longitudinally slidably and flowtightly received. Advantageous is a sealing at the rear end of the cuff, so that blood flows along the catheter guide are prevented. This seal may be a cap of latex or a similar material which surrounds the cuff at the end remote from the catheter tips, with a respective passage opening for each individual catheter.

A further advantageous embodiment of the invention is characterized in that the one catheter is provided with a conically tapering tip and with perforations in the region of this tip. This individual catheter is advantageously used for returning blood into the blood vessel.

A further advantageous embodiment resides in that the tip of the other individual catheter, which is advantageously the individual catheter used for removal of blood, is provided with an inclination and/or lateral openings.

It is also of advantage to provide at least one of the individual catheters with a scale and the other individual catheter with a marking permitting a control of the positions of the two catheters relative to one another, and to provide in the region of the extra-corporeal ends of both individual catheters parts of a latex or a similar material having flow paths which can be squeezed shut via hose clamps.

Finally, the aforementioned ends of the individual catheters may also be closed via strippable caps of latex or a similar material and the bottoms of these caps may be provided with a wall thickness reduction for the perforating insertion of a guidance spiral.

Based upon the enclosed drawing, an embodiment of the invention and the intended use of the double catheter shown as the exemplary embodiment, will hereafter be described. Shown in schematic views are:

FIG. 1 an overview of a double-barrelled relatively movable catheter;

FIG. 2 in a view similar to FIG. 1, the individual catheter alone which serves for blood supply and is provided with a scale;

FIG. 3 also in a view as in FIG. 1, the individual catheter serving the blood removal, by itself and with the associated longitudinal guide;

FIG. 4 is a cross-section through the region of the longitudinal guide of the double catheter according to line IV—IV in FIG. 3;

FIG. 5 the catheter tip of the double catheter by itself, in a perspective view;

FIG. 6 a cap by itself, in longitudinal section, serving as a seal in the region of the end of the longitudinal guide which is remote from the catheter tip;

FIG. 7 in a view like FIG. 6 a further cap for closing the extra-corporeal catheter ends; and FIG. 8 is a principle sketch showing the intended use of the double catheter.

In the double catheter, which in toto is designated with 10, the individual catheters 11, 12 are associated to be shiftable in direction of their elongation. The catheter 12 is formed of one piece with a guidance cuff 13 in which the other catheter 11 is received and which thus forms a longitudinal guide, so that the two individual catheters 11, 12 are shiftable relative to one another in direction of their elongation, but are fixable in any desired relative positions. At its rear end, i.e. the one remote from the catheter tips, this longitudinal guide is surrounded by a cap 14 of latex or a similar material as a seal against the passage of blood through the catheter guide, in the rear wall of which there are two passage openings 15, 16 through which the extra-corporeal ends of the individual catheters extend and are sealingly embraced by the edges bounding these openings.

The tip of the individual catheter 12 provided with the longitudinal guide 13, which is remote from the cap 14, is provided with an inclination 18 and two lateral holes 19. The tip 20 of the other individual catheter 11 is conically configured and in addition to an axial opening has at its free end perforations 21 in the conically converging tip region. Further, the individual catheter 11 is provided with a scale 22. Finally, both individual catheters 11, 12 have in the region of their extra-corporeal ends each a part 24, 25 of latex or similar material, which can be squeezed together with applyable clamps, which permits a squeezing shut of the flow paths. Following these parts there are parts 26, 27 which in a manner here not of interest are connectable with hose lines serving for blood removal respectively blood supply and which are closed by caps 28 which can be stripped off and which have a wall thickness reduction in the cap bottom.

In use of the inventive double catheter 10 a skin incision of appropriate size is made by means of a scalpel above a vein to be punctured and through this the vein is punctured in known manner by means of a puncture needle. Thereafter, as also known, a guidance spiral is to be introduced over the appropriate length into the punctured vein, and finally the individual catheter 11 is to be introduced via the same into the vein; if necessary, the bottom of the cap 28 is penetrated in the region of the wall thickness reduction. Thereafter, the second individual catheter 12 is pushed with the longitudinal guide 13 over the individual catheter 11 inserted into the vein, until an insertion depth is obtained which corresponds to the requirements; during this, the vein puncture location is enlarged according to the thickness of the longitudinal guide. Now the guidance spiral serving for insertion of the first catheter 11 can be withdrawn, the second catheter 12 with its longitudinal guide 13 be fixed by means of a seam, and finally the first catheter be further inserted into the vein according to the requirements. This concludes the insertion of the double catheter into a vein and the individual catheters are connectable in a manner which is known and here not of further interest, to a dialysis system via hose lines.

FIG. 8 shows diagrammatically the use of the inventive double catheter. The skin 30 is provided at 31 above a body vein 32, with an incision of appropriate size by means of a scalpel, and the vein is punctured at 33 by means of a puncture needle through the incision. In the above described manner a guidance spiral was thereafter inserted through the skin incision 31 and puncture location 33 and after removal of the puncture needle the individual catheter 11 was inserted via this guidance spiral into the vein. Thereafter the pushing-on of the second catheter was effected via the longitudinal guide 13 onto the first catheter 11, whereby the puncture 33 was enlarged according to the cross-section of the longitudinal guide. Thereafter the guidance spiral was removed and the second catheter with the longitudinal guide 13 was fixed in the position shown in the drawing in a not illustrated manner. Thereafter the individual catheter 11, having served as the guide for pushing-on of the second catheter 12, was shifted in the longitudinal guide and accordingly its catheter tip 20 advanced within the vein in the flow direction of blood flowing in the vein, as indicated by the arrow 34, so that the tip 20 of the individual catheter 11 is located in the flow direction of the blood forwardly of the tip having the inclination 18 on the second individual catheter. The catheter 12 provided with the longitudinal guide 13 serves for blood removal. The blood removal is effected in flow direction according to arrow 34, ahead of the tip 20 of the individual catheter 12 as indicated by the reversing arrow 35, whereafter the blood is guided to a dialysis system in a manner not of further interest here.

The blood flowing back from this system is re-introduced into the vein via the catheter 11 and exits into the vein in the region of the conical tip 20 through the axial opening according to arrow 36 as well as via the perforations in the conical tip region of this catheter. In view of the fact that the outlet opening 11 of the catheter 11 is located a substantial distance ahead of the blood removal location, in the blood flow direction, mixing of the blood returned from the dialysis system with the blood removed via the catheter 12 is effectively prevented.

I claim:

1. Catheter with two lumens for puncturing blood vessels, particularly in hemodialysis, comprising: two separate channels, one of each channels for supplying blood to, and the other for returning blood from, external circulation; said channels running side by side through a section with a point that can be inserted through a puncture into the blood stream and being axially separated at the other end; a longitudinal guide; each channel comprising an individual catheter slidable back and forth against the other channel inside said longitudinal guide; each channel being positionable at a predetermined location relative to the other channel dependent upon predetermined conditions.

2. Double catheter according to claim 1, wherein said longitudinal guide comprises a cuff surrounding and connected to one catheter in which the other catheter is longitudinally slidably received.

3. Double catheter according to claim 2, wherein said longitudinal guide with one catheter is of one-piece construction.

4. Double catheter according to claim 2 or 3, including a seal at said cuff end remote from the catheter tips for preventing blood from flowing along the catheter guide in said cuff.

5. Double catheter according to claim 4, wherein said seal comprises a cap of latex material surrounding said cuff with a respective passage opening for each individual catheter.

6. Double catheter according to claim 1, wherein one catheter has a conically tapering tip and perforations in the region of said tip.

7. Double catheter according to claim 1, wherein one catheter has a tip with an inclination and lateral openings.

8. Double catheter according to claim 1, wherein at least one of the individual catheters has a scale and the other individual catheter has a marking for controlling the relative position of the two catheters.

9. Double catheter according to claim 1, wherein the individual catheters have regions of extra-corporeal ends with parts of latex, cross-sections in the region of said parts being squeezably closable by clamps.

10. Double catheter according to claim 1, wherein the individual catheters have extra-corporeal ends which are closable by strippable caps of latex.

11. Double catheter according to claim 10, said caps have bottoms with a wall thickness reduction for perforating insertion of a guidance spiral.

12. Double catheter according to claim 1, wherein a guidance spiral is introduced over a predetermined length into a punctured vein, one individual catheter being introduced via said guidance spiral into said vein, the other individual catheter being pushed with said longitudinal guide over said one individual catheter until a predetermined insertion depth is obtained, the vein puncture location being enlarged according to the thickness of said longitudinal guide, said guidance spiral serving for insertion of said one catheter being thereafter withdrawn, said one catheter being further insertable into said vein dependent on predetermined conditions.

13. Double catheter according to claim 12, wherein said longitudinal guide comprises a cuff surrounding and connected to one catheter in which the other catheter is longitudinally slidably received; said longitudinal guide with one catheter being of one-piece construction; a seal at said cuff end remote from the catheter tips for preventing blood from flowing along the catheter guide in said cuff; said seal comprising a cap of latex material surrounding said cuff with a respective passage opening for each individual catheter; one catheter having a conically tapering tip and perforations in the region of said tip; said one catheter having a tip with an inclination and lateral openings; at least one of the individual catheters having a scale and the other individual catheter having a marking for controlling the relative position of the two catheters; the individual catheters having regions of extra-corporeal ends with parts of latex, cross sections in the region of said parts being squeezably closable by clamping means.

* * * * *